(12) United States Patent
Robertson

(10) Patent No.: US 8,579,802 B2
(45) Date of Patent: Nov. 12, 2013

(54) FLEXIBLE ENDOSCOPE WITH MODIFIABLE STIFFNESS

(75) Inventor: David W. Robertson, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 327 days.

(21) Appl. No.: 12/915,545

(22) Filed: Oct. 29, 2010

(65) Prior Publication Data

US 2011/0106055 A1 May 5, 2011

Related U.S. Application Data

(60) Provisional application No. 61/257,299, filed on Nov. 2, 2009.

(51) Int. Cl.
*A61B 1/00* (2006.01)
*A61B 1/04* (2006.01)

(52) U.S. Cl.
USPC .......................... 600/144; 600/104; 600/114

(58) Field of Classification Search
USPC ............... 600/104, 144, 146, 434–435, 114, 600/139–143, 145
See application file for complete search history.

(56) References Cited

U.S. PATENT DOCUMENTS

| | | | |
|---|---|---|---|
| 5,168,864 A | 12/1992 | Shockey | |
| 5,308,342 A * | 5/1994 | Sepetka et al. | 604/525 |
| 5,702,754 A | 12/1997 | Zhong | |
| 5,759,151 A | 6/1998 | Sturges | |
| 6,048,620 A | 4/2000 | Zhong | |
| 6,296,608 B1 | 10/2001 | Daniels et al. | |
| 6,984,203 B2 | 1/2006 | Tartaglia et al. | |
| 7,004,938 B2 * | 2/2006 | Ormsby et al. | 606/33 |
| 2004/0015151 A1 | 1/2004 | Chambers | |
| 2006/0258987 A1 | 11/2006 | Lentz et al. | |
| 2006/0264907 A1 | 11/2006 | Eskridge et al. | |
| 2008/0300462 A1 | 12/2008 | Intoccia et al. | |
| 2009/0112226 A1 | 4/2009 | Self et al. | |
| 2009/0192495 A1 | 7/2009 | Ostrovsky et al. | |

OTHER PUBLICATIONS

International Search Report and Written Opinion for International Application No. PCT/US2010/054685, mailed on Jun. 17, 2011, (15 pages).
Invitation to Pay Additional Fees and Partial International Search Report in International Application No. PCT/US2010/054685, mailed on Jan. 31, 2011, (7 pages).

* cited by examiner

*Primary Examiner* — Alireza Nia
(74) *Attorney, Agent, or Firm* — Bookoff McAndrews, PLLC

(57) ABSTRACT

An apparatus includes a flexible elongate member that defines a lumen and is configured to be inserted within a body passageway of a patient. The flexible elongate member includes a proximal portion, a distal portion, and a medial portion disposed between the proximal portion and the distal portion. The distal portion is movable between a substantially linear configuration and a curved configuration. A stiffening member is coupled to the flexible elongate member. The stiffening member is movable to a selected location along a length of the flexible elongate member to provide modified flexibility to the selected location of the flexible elongate member. The stiffening member may include a first portion and a second portion, the first portion having a first stiffness and the second portion having a second stiffness different than the first stiffness. The stiffening member may be disposed within a lumen or at an exterior portion of the flexible elongate member.

10 Claims, 14 Drawing Sheets

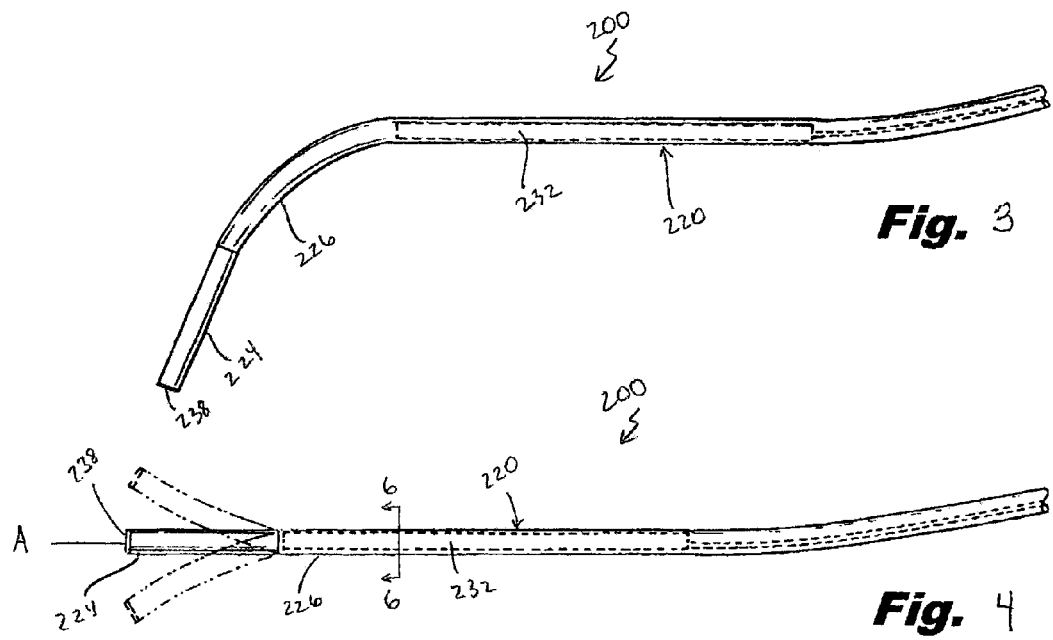
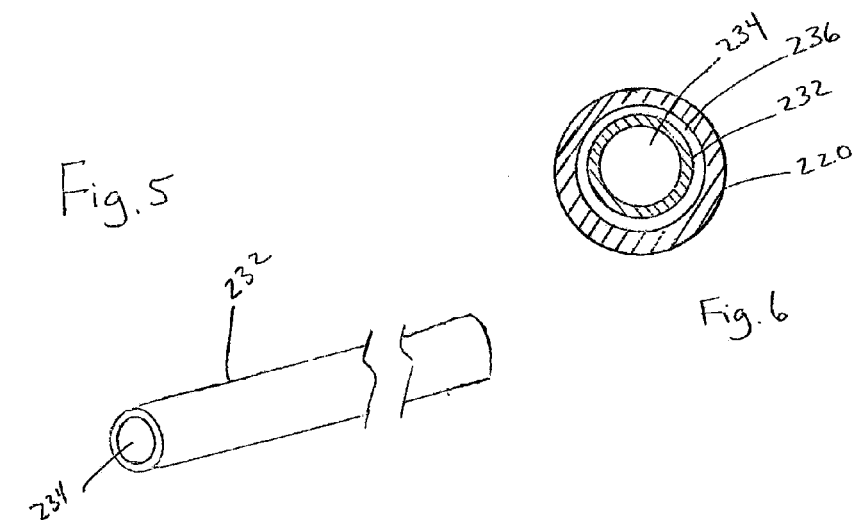

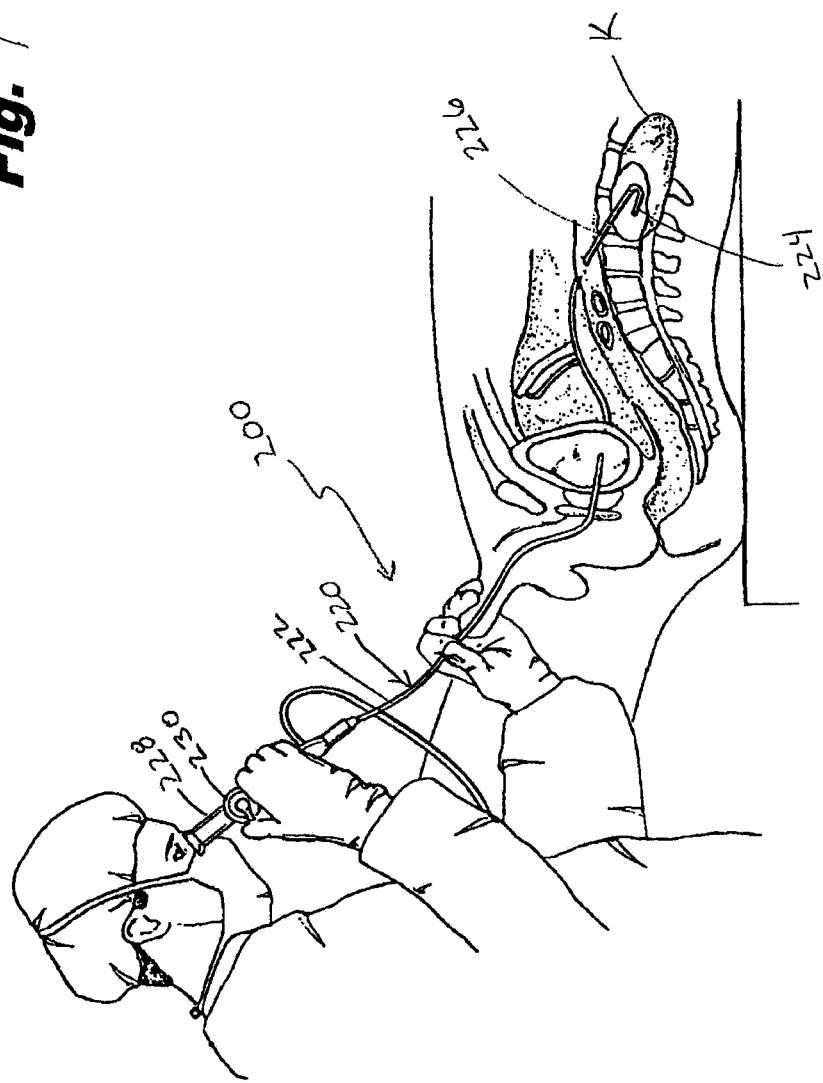

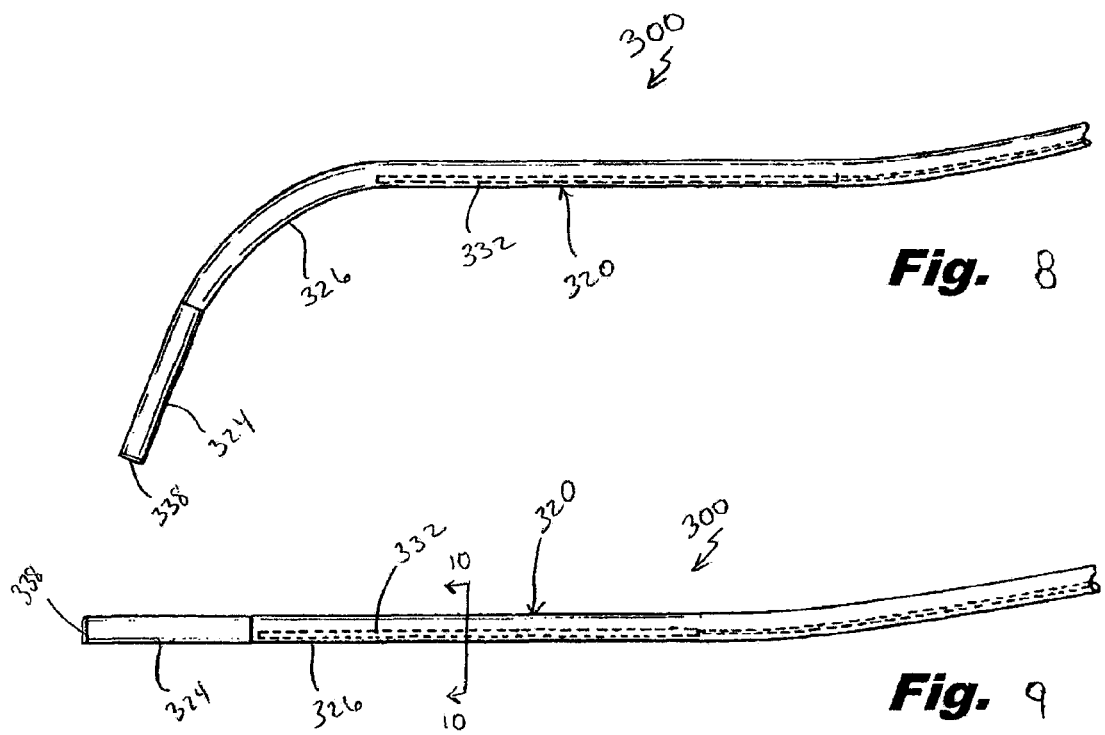
Fig. 8
Fig. 9
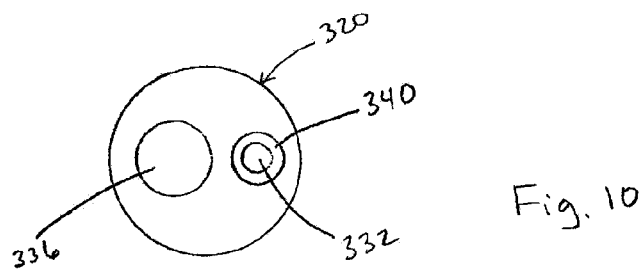
Fig. 10

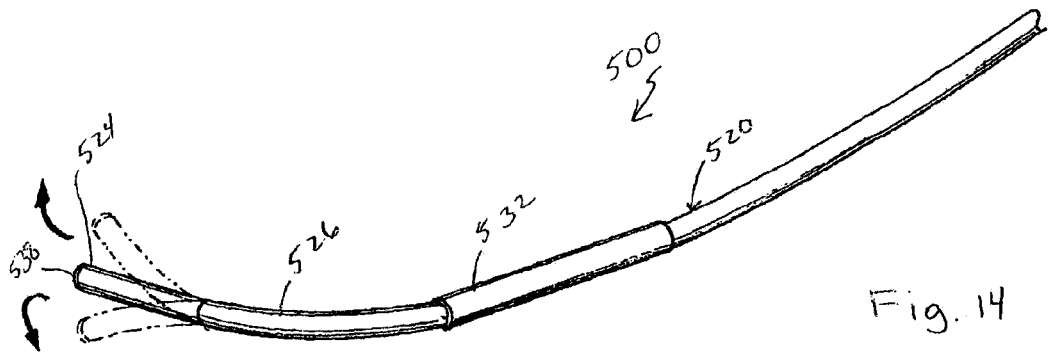
Fig. 14
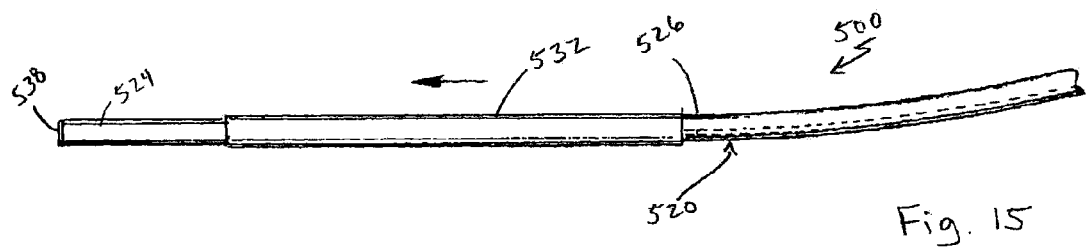
Fig. 15
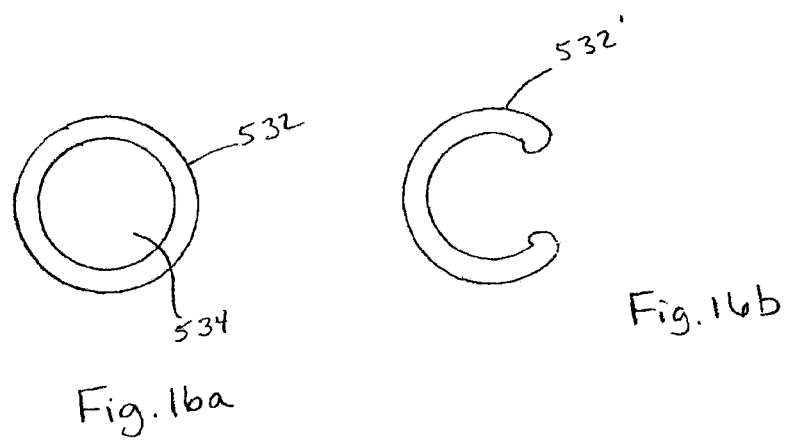
Fig. 16a
Fig. 16b

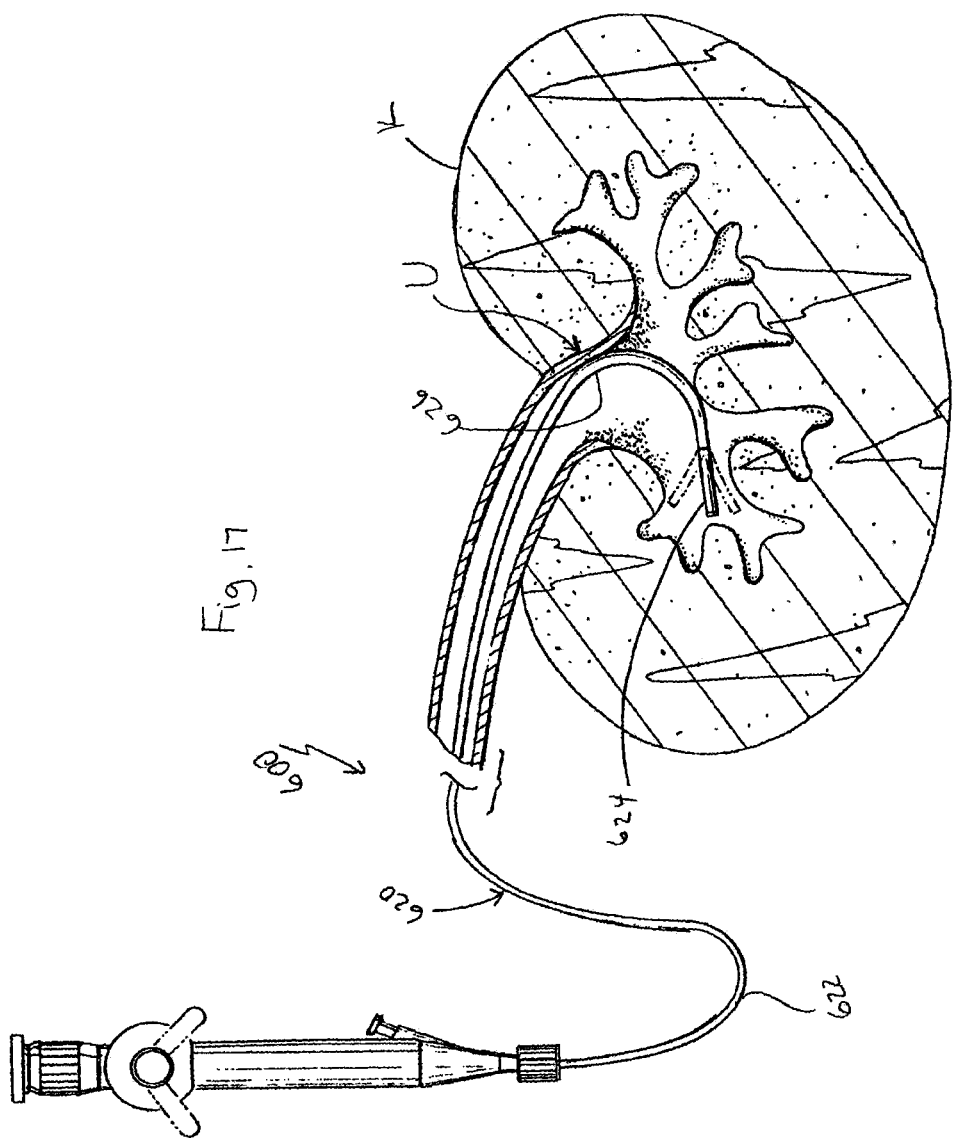

FLEXIBLE ENDOSCOPE WITH MODIFIABLE STIFFNESS

CROSS REFERENCE TO RELATED APPLICATION

This Nonprovisional Patent Application claims the benefit of priority under 35 U.S.C. §119 to U.S. Provisional Patent Application No. 61/257,299, filed Nov. 2, 2009, and titled "FLEXIBLE ENDOSCOPE WITH MODIFIABLE STIFFNESS," which is incorporated herein by reference.

TECHNICAL FIELD

The present invention generally relates to medical devices such as endoscopes and catheters. More specifically, the invention relates to flexible medical devices with modifiable stiffness.

BACKGROUND INFORMATION

A variety of medical devices are commonly used to access remote regions of the body to deliver diagnostic or therapeutic agents and to perform surgical procedures on those regions. For example, flexible endoscopes can use various body passageways (such as the alimentary and excretory canals and airways) to access the colon, esophagus, stomach, urethra, bladder, ureter, kidney, lungs, bronchi, uterus, and other organs. Catheters may use the circulatory system as pathways to access treatment sites near the heart.

These medical devices are often introduced into the body through a large artery such as those found in the groin or in the neck, through the anus to access the colon and intestinal tract, or through the urethra to access the urinary system. The devices are often passed through ever-narrower arteries and canals until they can reach the operative site inside the body. Many such pathways may curve, loop around, and even wind back. In order to navigate the medical device through the pathways to the operative site, the medical device must be flexible to allowing bending, yet have enough column strength to prevent buckling of the medical device as it is pushed.

Some endoscopes and electrophysiology catheters can steer or deflect the distal tip of the endoscope to follow the pathway of the anatomy under examination such as the colon, bladder, kidney, and heart. Deflection or articulation is often a desirable characteristic in these types of medical devices to minimize friction force and trauma to the surrounding tissue, and to survey targeted examination sites. Navigation of the endoscope through various areas within a patient improves the success of the examination and minimizes pain, side effects, risk, or sedation to the patient.

In some known devices, to achieve active deflection at the distal flexible portion of the device, the endoscope may use a force created on one end of the device, usually at a handle. The force is then transmitted to the articulation section by control cables or pull-wires. The pull-wires are carried within the endoscope shaft connecting the distal end to a set of controls in the handle. By manipulating the controls, the operator is able to steer the distal end portion of the endoscope during insertion and direct it to a region of interest within the body of the patient.

In some situations, it may be desirable to provide one or more rigid portions of the endoscope along its length. For example, it may be desirable to modify the flexibility of (e.g., strengthen or make more rigid) a selected portion of the endoscope such as, for example, just proximal to a deflectable distal end portion. Such a feature may provide better control and maneuverability of the endoscope within the body of a patient.

In some situations, it may be desirable to provide deflection or articulation of more than just the deflectable distal end portion of an endoscope. For example, it may be desirable to add a secondary or passive deflection portion proximal of the active deflection portion (e.g., distal end portion).

SUMMARY OF THE INVENTION

The invention relates generally to a flexible medical device configured to be inserted into a body lumen of a patient. The medical device provides improved maneuverability and functionality for use during surgical procedures such as endoscopic procedures.

In one aspect, the invention involves an apparatus that includes a flexible elongate member that may define at least one lumen and may be configured to be inserted within a body passageway of a patient. The flexible elongate member may include a proximal portion, a distal portion, and a medial portion disposed between the proximal portion and the distal portion. The distal portion may be movable between a substantially linear configuration and a curved configuration. A stiffening member may be coupled to the elongate member. The stiffening member may be movable to a selected location along a length of the elongate member to modify the flexibility of the selected location of the elongate member. The stiffening member may also include a first portion and a second portion, the first portion having a first stiffness and the second portion having a second stiffness, different than the first stiffness.

Embodiments according to this aspect of the invention can include the following features. The stiffening member may be disposed within the at least one lumen of the flexible elongate member. The stiffening member may include a first sleeve and a second sleeve telescopically coupled to one another. The stiffening member may have a variable diameter along a length of the stiffening member. The stiffening member may have a varying wall thickness along a length of the stiffening member. The stiffening member may be configured to be slidably coupled to an exterior surface of the flexible elongate member.

In another aspect, the invention involves an apparatus that includes a flexible elongate member that may define a lumen and may be configured to be inserted within a body passageway of a patient. The flexible elongate member may include a proximal portion, a distal portion, and a medial portion disposed between the proximal portion and the distal portion. The distal portion may be movable between a substantially linear configuration and a curved configuration. A stiffening member may be disposed within the lumen of the elongate member. The stiffening member may also define a lumen. The lumen of the flexible elongate member and the lumen of the stiffening member may collectively define a working channel configured to slidably receive a medical instrument therethrough.

Embodiments according to this aspect of the invention can include the following features. The stiffening member may include a first sleeve and a second sleeve telescopically coupled to one another. The stiffening member may have a variable diameter along a length of the stiffening member. The stiffening member may have a varying wall thickness along a length of the stiffening member. The stiffening member may be configured to be movable to a selected location along a length of the elongate member to modify the flexibility of the selected location of the elongate member. The lumen of the flexible elongate member may be a first lumen and the flexible elongate member may define a second lumen configured to receive a medical instrument therein. The stiffening member may include a first portion and a second portion. In such an embodiment, the first portion may have a first stiffness and the second portion may have a second stiffness different than the first stiffness.

In another aspect, the invention involves an apparatus that includes a flexible elongate member configured to be inserted within a body passageway of a patient. The flexible elongate member may define a lumen and may include a proximal portion, a distal portion, and a medial portion between the proximal portion and the distal portion. The distal portion may be steerable between a first configuration and a second configuration. A sleeve may be coupled to the flexible elongate member such that at least a portion of the flexible elongate member is disposed within a lumen of the sleeve. The sleeve and the flexible elongate member may be configured to be slidably movable relative to each other. At least a portion of the medial portion of the flexible elongate member may be formed with a shape memory material and may have a curved configuration. The at least a portion of the medial portion of the flexible elongate member may be movable from the curved configuration when unrestrained to a restrained configuration when the medial portion is disposed within the lumen of the sleeve.

Embodiments according to this aspect of the invention can include the following features. The apparatus may further include a stiffening member coupled to the flexible elongate member. In some such embodiments, the stiffening member may be configured to be slidably movable to a selected location along a length of the elongate member to modify the flexibility of the selected location of the elongate member. In some such embodiments, the stiffening member may be disposed within the lumen of the flexible elongate member. In some such embodiments, the stiffening member may include a first sleeve and a second sleeve telescopically coupled to one another. In some such embodiments, the stiffening member may have a variable diameter along a length of the stiffening member. In some such embodiments, the first configuration may be substantially linear and the second configuration may curved. In some such embodiments, the stiffening member may be configured to be slidably coupled to an exterior of the flexible elongate member.

BRIEF DESCRIPTION OF THE DRAWINGS

A fuller understanding of the aspects, objects, features, and advantages of certain embodiments according to the invention will be obtained and understood from the following description when read together with the accompanying drawings, which primarily illustrate the principles of the invention and embodiments thereof. The drawings are not necessarily to scale and like reference characters denote corresponding or related parts throughout the several views. The drawings and the disclosed embodiments of the invention are exemplary only and not limiting on the invention.

FIG. 3 is a side view of a portion of the medical device of FIG. 2 shown in a first configuration.

FIG. 4 is a side view of the portion of the medical device of FIG. 3 shown in a second configuration.

FIG. 5 is a side perspective view of a stiffening member according to an embodiment.

FIG. 6 is a cross-sectional view of the medical device of FIG. 2 taken along line 6-6 in FIG. 4.

FIG. 7 illustrates the medical device of FIG. 2 shown in use disposed within a body of a patient.

FIG. 8 is a side view of a portion of a medical device according to another embodiment, shown in a first configuration.

FIG. 9 is a side view of the portion of the medical device of FIG. 8 shown in a second configuration.

FIG. 10 is a cross-sectional view of the medical device of FIGS. 8 and 9 taken along line 10-10 in FIG. 9.

FIG. 14 is a side view of a portion of a medical device according to another embodiment, shown in a first configuration.

FIG. 15 is a side view of a portion of the medical device of FIG. 14 shown in a second configuration.

FIGS. 16a and 16b are each a cross-sectional view of a stiffening member according to different embodiments.

FIG. 17 is a schematic illustration of a kidney and a medical device according to one embodiment.

DESCRIPTION

Figure 1:
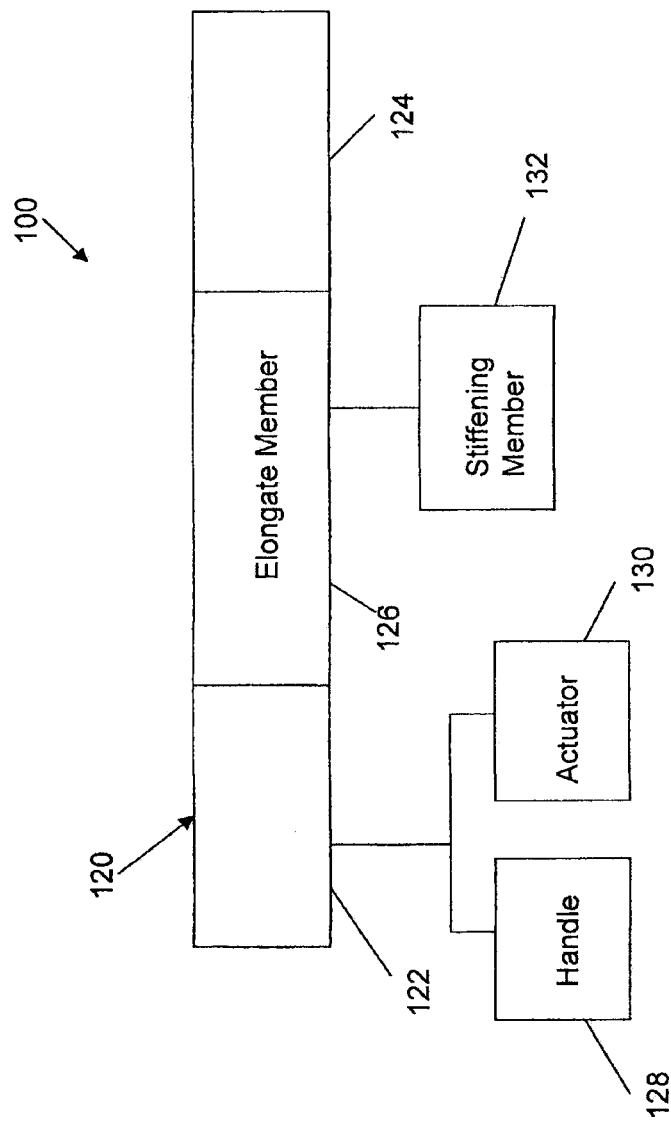
FIG. 1 is a schematic illustration of a medical device according to an embodiment.
Figure 2:
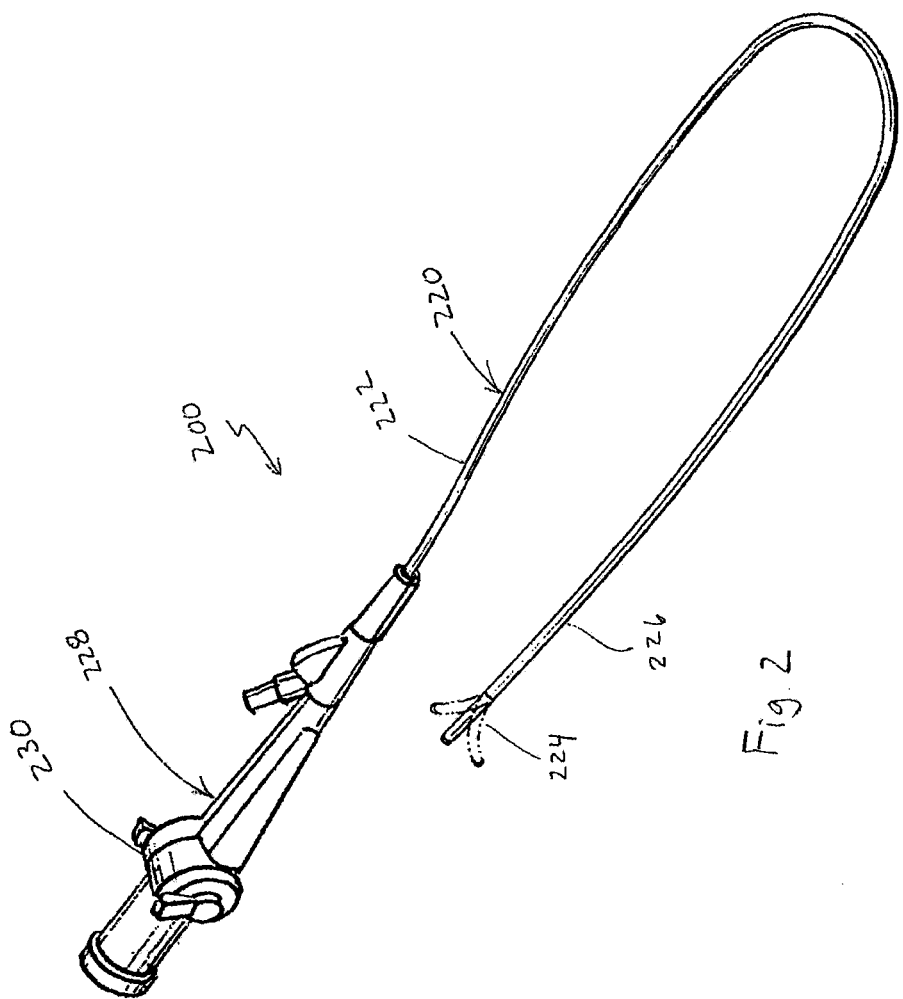
FIG. 2 is a perspective view of an embodiment of a medical device.
Figure 11:
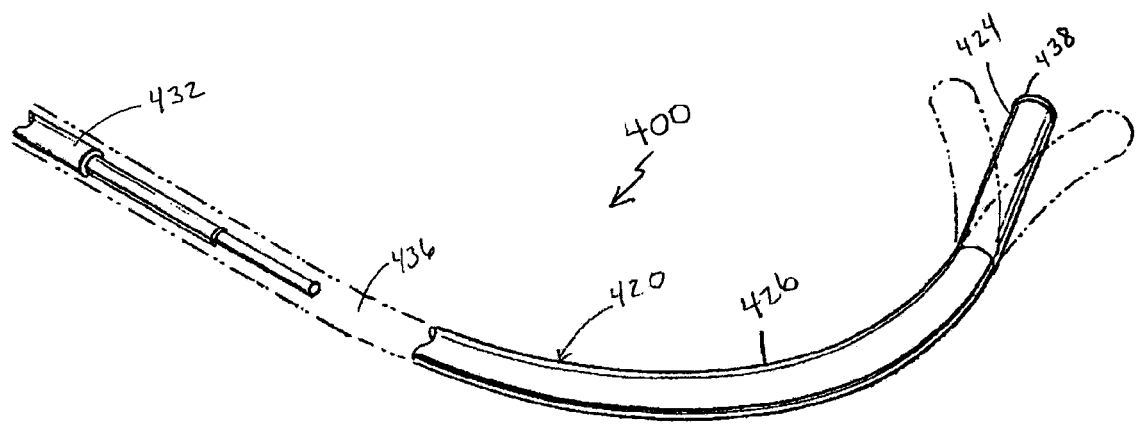
FIG. 11 is a side view of a portion of a medical device according to another embodiment, shown in a first configuration.

As indicated above, the invention relates to a flexible structure with modifiable stiffness for use as part of a medical device such as, for example, endoscopes, ureteroscopes, and catheters. These medical devices allow an operator to access and view internal body anatomy of a patient as well as to insert surgical instruments such as biopsy forceps, graspers, baskets, snares, fulguration probes, and other tools into the patient's body. In addition, these devices may include integrated diagnostic and therapeutic capabilities to allow the operator to treat the patient in a single procedure. An endoscope may provide visualization and/or illumination, via fiber optics or digital imaging chips, that may be either integrated or slidably removable from a lumen.

Access into various anatomy such as, for example, a ureter, with a flexible ureteroscope can sometimes require special techniques. The flexibility of the instrument may necessitate the use of an additional device to guide or pass an endoscope through a body lumen. One commonly used device is a guide wire that can be placed within a lumen of the ureteroscope and used to guide the ureteroscope to a desired location in the patient's body. Another commonly used tool is an access cannula or sheath through which an endoscope can be inserted.

Some endoscopes and electrophysiology catheters can steer or deflect the distal tip of the endoscope to follow the pathway of the anatomy under examination such as the colon, bladder, kidney, and heart. To achieve active deflection at the distal flexible portion of the device, some endoscopes use a force created on one end of the device, usually at a handle, which is then transmitted to an articulatable or deflectable section by control cables or pull-wires. By manipulating the controls, the operator is able to steer the distal portion of the endoscope during insertion and direct it to a region of interest within the body of the patient.

As described herein, in some embodiments, a flexible medical device, such as an endoscope, can include a steerable deflectable distal end portion that is movable between a substantially linear or straight configuration to multiple different curved configurations. Such deflection of a distal end portion is sometimes referred to as active deflection as it is achieved through actuating the distal end portion with an actuator or other mechanism. Such an actuator is typically disposed at a proximal end of the device, such as on a handle of the device. In some embodiments, as described herein, a medical device can also include what is referred to as a passive or a secondary deflectable portion. In some embodiments, a medical device can include a strengthening or stiffening member coupled to a flexible elongate member. As described in more detail below with reference to specific embodiments, the stiffening member can be moved or positioned at a selected location along a length of the flexible elongate member to modify the flexibility (e.g., strengthen or make more rigid) of a selected portion or section of the flexible elongate member. Thus, the flexibility of the elongate member can be modified along a length of the elongate member.

As used herein, the words "proximal" and "distal" refer to direction closer to and away from, respectively, an operator (e.g., surgeon, physician, nurse, technician, etc.) who would insert the disclosed flexible elongate member into the patient, with the distal end of the device inserted first into a patient's body. The end of an endoscope inserted first inside a patient's body would be the distal end of the device, and the end of the device closest to the operator and to an exterior incision or opening in the patient's body would be the proximal end of the device.

FIG. 1 is a schematic representation of a medical device (also referred to herein as "endoscope" or "apparatus") according to an embodiment of the invention. An endoscope 100 includes an elongate member 120 that can be inserted at least partially into a body of a patient (not shown in FIG. 1). The elongate member 120 can be flexible, or can include a portion that is flexible, to allow the elongate member 120 to be maneuvered within the body. The elongate member 120 can be uniformly flexible or can include a plurality of segments having varying degrees of flexibility or rigidity. The endoscope 100 can be inserted into a variety of different body lumens or cavities, such as, for example, a ureter, a gastrointestinal lumen, an esophagus, a vascular lumen, etc. The elongate member 120 includes a proximal end portion 122, a distal end portion 124 and a medial portion 126 disposed between the proximal end portion 122 and the distal end portion 124.

The endoscope 100 can optionally include an outer sleeve (not shown) disposed on an outer surface of the flexible elongate member 120 to provide a smooth exterior surface. The outer sleeve can be coated with a hydrophilic, lubricious coating such as HYDROPASS™ hydrophilic coating available from Boston Scientific Corporation, of Natick, Mass., and described in U.S. Pat. Nos. 5,702,754 and 6,048,620, which are herein incorporated by reference. In some embodiments, the exterior of the flexible elongate member 120 can be provided with such a smooth exterior surface.

The endoscope 100 can also include a handle 128 coupled to the elongate member 120. The handle 128 is configured to be disposed outside the body of the patient and can include one or more control mechanisms or actuators 130 that can be used to control and maneuver the elongate member 120 through the body lumen. For example, the distal end portion 124 can be deflectable and can be actuated between a substantially linear configuration and a curved, angled or bent configuration. The distal end portion 124 can be moved to a variety of different curved, angled or bent configurations in a variety of different directions relative to a longitudinal axis of the elongate member 120. As discussed above, such deflection of the distal end portion 124 is referred to herein as active deflection because it is moved between its various configurations through the use of an actuator or other mechanism. Example of various endoscopes with a deflectable distal end portion are described in U.S. patent application Ser. No. 12/127,261 (Patent App. Pub. No. 2008/0300462) and U.S. patent application Ser. No. 12/358,624, the disclosures of which are hereby incorporated by reference in their entireties. Other known mechanisms used to deflect a distal end portion of an endoscope can alternatively be used.

The endoscope 100 can optionally include one or more lumens (not shown in FIG. 1) extending through the elongate member 120 and/or handle 128. In some embodiments, the endoscope 100 includes a single lumen through which various components can be received. For example, optical fibers or electrical wires (not shown in FIG. 1) can pass through a lumen of the endoscope 100 to provide illumination and/or imaging capabilities at a distal end portion of the endoscope 100. The endoscope 100 can also be configured to receive various medical devices or tools (not shown in FIG. 1) through one or more lumens (not shown in FIG. 1) of the endoscope 100, such as, for example, irrigation and/or suction devices, forceps, drills, snares, needles, etc. An example of such an endoscope with multiple lumens is described in U.S. Pat. No. 6,296,608 to Daniels et, al., the disclosure of which is incorporated herein by reference in its entirety. In some embodiments, a fluid channel (not shown in FIG. 1) is defined by the endoscope 100 and coupled at a proximal end portion to a fluid source (not shown in FIG. 1). The fluid channel can be used to irrigate an interior of a body lumen. In some embodiments, an eyepiece (not shown in FIG. 1) can be coupled to a proximal end portion of the endoscope 100, for example, adjacent the handle 128, and coupled to an optical fiber (or other imaging or viewing device) that can be disposed within a lumen of the endoscope 100. Such an embodiment allows a physician to view the interior of a body lumen through the eyepiece.

In some embodiments, a stiffening member 132 (also referred to as "strengthening member") can be coupled to the elongate member 120 to provide modify the flexibility (e.g., provide strength or rigidity) of a selected portion of the elongate member 120. For example, the stiffening member 132 can be slidably coupled to the elongate member 120 such that the stiffening member 132 can be slidably moved to a desired location along a length of the elongate member 120. The elongate member 120 can then have some portions that are more rigid and/or flexible than others. For example, the portion of the elongate member 120 associated with, or located adjacent to, the stiffening member 132 can be more rigid or stiff than other portions of the elongate member 120. It may be desirable, for example, to strengthen or otherwise modify the flexibility of a portion of the elongate member 120 just proximal of the deflectable distal end portion 124. Such modification can provide better maneuverability and control of the distal end portion 124 of the elongate member 120.

The stiffening member 132 can be coupled to the elongate member 120 with, for example, a friction fit such that the stiffening member 132 can slide relative to the elongate member 120 and maintain a desired position along the length of the elongate member 120. It should be understood, however, that other coupling methods can be used. For example, the stiffening member 132 can be coupled to the elongate member 120 using a clip, clamp or other known coupling methods. The stiffening member 132 can alternatively be fixedly secured at a selected location on the elongate member 120. The stiffening member 132 can be configured to be manually moved along the flexible elongate member 120, or alternatively, the endoscope can include a mechanism with controls, for example, on the handle 128 configured to move the stiffening member 132 along the flexible elongate member 120.

The stiffening member 132 can be a variety of different shapes, sizes and configurations as described in more detail below with reference to specific embodiments. In some embodiments, the stiffening member 132 is disposed within a lumen of the elongate member 120. In such an embodiment, the stiffening member 132 can be configured as a solid rod or have a sleeve configuration (e.g., defines an internal lumen). In some embodiments, the stiffening member 132 can be configured as a coil or spring disposed within a lumen of the elongate member 120. In some embodiments, the stiffening member 132 is disposed within a working lumen or channel of the elongate member 120. For example, if the stiffening member 132 defines a lumen and is disposed within the lumen of the elongate member 120, a medical tool, such as a snare or forceps, can be inserted through the working lumen of the elongate member 132 and also through the lumen of the stiffening member 132. In some embodiments, the elongate member 120 includes two or more lumens, and the stiffening member 132 is disposed within a first lumen of the elongate member 120 and additional lumens are used as a working channel for insertion of a medical tool, such as a snare or forceps; to insert imaging and illumination devices; or provide irrigation fluids or insufflation gases. In some embodiments, the stiffening member 132 is configured to be inserted into a lumen of the elongate member 120 during insertion of the elongate member 120 into a patient's body and then removed from the elongate member 120 prior to another medical procedure being performed using the endoscope.

In some embodiments, the stiffening member 132 can provide varying rigidity or stiffness along its length. Thus, when the stiffening member 132 is coupled to the elongate member 120, the stiffening member 132 can provide varying rigidity and/or flexibility to different portions of the elongate member 120. For example, the stiffening member 132 can have a varying wall thickness along its length such that some portions of the stiffening member 132 are stiffer or more rigid than other portions. In some embodiments, the stiffening member 132 can be tapered along an exterior of the stiffening member 132 (e.g., the outer diameter varies along a length of the stiffening member). The stiffening member 132 can alternatively, or in addition to, have interior walls that are tapered (e.g., the inner diameter varies along the length of the stiffening member). In some embodiments, the stiffening member 132 can have varying diameters or wall thicknesses at stepped locations or sections along its length.

In some embodiments, the stiffening member 132 can include multiple components telescopically coupled together. In such an embodiment, the telescoping members can allow the user to modify the length and flexibility (e.g., rigidity or strength) of the stiffening member 132 by collapsing or extending the telescoping components. For example, to allow for a shorter stiffening member 132, one or more telescoping components can be collapsed relative to each other (e.g. one component slidably received within another). Extending or collapsing the telescoping components can also provide varying stiffness or strength of the stiffening member 132 along its length. For example, a first smaller diameter telescoping component that can be received within a second larger diameter telescoping component may be less rigid than the larger diameter component. Thus, if the two components are extended relative to each other, the portion of the elongate member 120 associated with (e.g., adjacent or near) the first smaller diameter component may be provided with more flexibility than the portion of the elongate member 120 associated with the second larger diameter component.

In some embodiments, a medical device 100 includes an elongate member 120 that includes a secondary or passive deflectable portion. For example, all or a portion of an elongate member 120 can be formed with a shape memory material, such as Nitinol, shape memory polymers, or other suitable shape-memory material. The shape-memory portion (e.g., secondary deflectable portion) of the elongate member 120 can have a biased curved configuration when unrestrained and allowed to assume its biased shape, and can be movable to, for example, a substantially linear or straight configuration when restrained, for example, within a lumen of a sleeve, sheath, cannula or with another type of restraining device or component. In some embodiments stiffening member 132 can be a shape memory material that has a biased curved configuration that causes medial portion 126 to deflect as stiffening member 132 is advanced into medial portion 126. For example, the stiffening member 132 can be moved through a stiffer proximal portion 122 where stiffening member 132 is restrained in a substantially straight configuration and then moved into a medial portion 126 that is less rigid allowing the biased curved configuration of the stiffening member 132 to deflect the medial portion 126. In some embodiments, it may be desirable to have a shape-memory portion disposed just proximally of the active deflectable distal end portion 124 of the elongate member 120. Such an embodiment is described below with reference to FIGS. 18-20.

Having described above various general examples, several examples of specific embodiments are now described. These embodiments are only examples, and many other configurations of an endoscope are contemplated.

FIGS. 2-5 illustrate an embodiment of a medical device according to an embodiment. An endoscope 200 includes a flexible elongate member 220 coupled to a handle 228. The flexible elongate member 220 (also referred to herein as "elongate member") includes a proximal end portion 222, a distal end portion 224 and a medial portion 226 between the proximal end portion 222 and the distal end portion 226. The length of the medial portion 226 can vary, but is generally referred to as the portion of the elongate member 220 between the proximal end portion 222 and the distal end portion 226. The elongate member 220 defines a lumen 236 (see e.g., FIG. 6) between the proximal end portion 222 and the distal end portion 224 that is in fluid communication with an opening (not shown) defined at a distal end 238 of the elongate member 220.

The distal end portion 224 is deflectable and can be actuated with an actuator 230 disposed on or coupled to the handle 228. The deflectable distal end portion 224 can be moved or articulated from a substantially linear or straight configuration (e.g., as shown in FIG. 3) to a variety of different curved or angled configurations in a variety of different directions relative to a longitudinal axis (e.g., centerline) of the elongate member 220, as shown in FIG. 4 (FIG. 4 illustrates two example curved or angled configurations shown in broken-line format). As discussed above, such deflection of the distal end portion 224 is referred to herein as active deflection because it is moved between its various configurations through the use of an actuator or other mechanism. Actuation of the deflectable distal end portion 224 can be achieved using a variety of different known mechanisms such as in the references incorporated by reference above.

The endoscope 200 also includes a stiffening member 232 that defines a lumen 234 (see e.g., FIG. 5). In this embodiment, the stiffening member 232 is disposed within the lumen 236 (see e.g., FIG. 6) of the elongate member 220 and can be slidably moved to a selected location along a length of the elongate member 220. For example, FIG. 3 shows the stiffening member 232 disposed at a first location within the lumen 236 of the elongate member 220 and FIG. 4 shows the stiffening member 232 disposed at a second location within the lumen 236 of the elongate member 220.

In use, the endoscope 200 can be inserted into a body of a patient to perform a medical procedure. FIG. 7 illustrates the endoscope 200 with the distal end portion 224 and a portion of the medial portion 226 disposed within a kidney K of a patient. As shown in FIG. 7, the distal end portion 224 can be maneuvered or steered to a desired location within the kidney K and is shown in a curved or angled configuration. The stiffening member 232 (not shown in FIG. 7) is disposed within the medial portion 226 just proximal of the distal end portion 224 to modify the flexibility (e.g., strengthen or make more rigid) of that portion of the elongate member 220. In this embodiment, a medical tool can be inserted through the lumen 236 of the elongate member 220 and through the lumen of the 234 of the stiffening member 232 and into the kidney K to perform a medical procedure.

FIGS. 8-10 illustrate a portion of an endoscope according to another embodiment. An endoscope 300 includes an elongate member 320 having a distal end portion 324, a proximal end portion (not shown) and a medial portion 326. The elongate member 320 defines a first lumen 336 (see e.g., FIG. 10) between the proximal end portion and the distal end portion 324 that is in fluid communication with an opening (not shown) defined at a distal end 338 of the elongate member 320. The lumen 336 can be used as a working channel for insertion of a medical tool. In this embodiment, the elongate member 320 also defines a second lumen 340 (see FIG. 10) in which a stiffening member 332 can be disposed. The endoscope 300 can also include a handle (not shown) and an actuator (not shown) as described above for previous embodiments.

As with the previous embodiments, the distal end portion 324 is deflectable and can function in the same manner as the distal end portions 124, 224 previously described, and can be moved or articulated from a substantially linear or straight configuration (e.g., as shown in FIGS. 8 and 9) to a variety of different curved, angled or bent configurations (not shown) in a variety of different directions relative to a longitudinal axis of the elongate member 320.

In this embodiment, the stiffening member 332 is in the form of a rod or can alternatively be a small sleeve or cannula (e.g., defining a lumen) that is slidably disposed within the lumen 340 of the elongate member 320. The stiffening member 332 can function in the same manner as described for previous embodiments to modify the flexibility of a selected portion of the elongate member 320. FIG. 8 illustrates the stiffening member 332 disposed at a first location within the lumen 336 of the elongate member 320, and FIG. 9 shows the stiffening member 332 disposed at a second location within the lumen 336 of the elongate member 320.

FIGS. 11-13e illustrate another embodiment of an endoscope. An endoscope 400 includes an elongate member 420 having a distal end portion 424, a proximal end portion (not shown) and a medial portion 426. The elongate member 420 defines a lumen 436 between the proximal end portion and the distal end portion 424 that is in fluid communication with an opening (not shown) defined at a distal end 438 of the elongate member 420. The lumen 436 can be used as a working channel for insertion of a medical tool. A stiffening member 432 is slidably disposable within the lumen 436 of the elongate member 420. The endoscope 400 can also include a handle (not shown) and an actuator (not shown) as described above for previous embodiments.

As with the previous embodiments, the distal end portion 424 is deflectable and can function in the same manner as the distal end portions 124, 224, 324 previously described, and can be moved or articulated from a substantially linear or straight configuration (e.g., as shown in FIGS. 13a-13e), to a variety of different curved or angled configurations (as shown in broken-line in FIG. 11) in a variety of different directions relative to a longitudinal axis of the elongate member 420.

Figure 12:
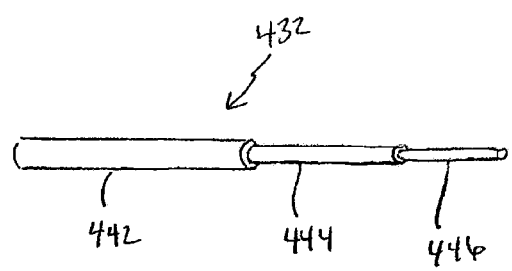
FIG. 12 is a aside view of a stiffening member according to an embodiment.

In this embodiment, the stiffening member 432 includes telescoping members 442, 444 and 446 as shown in FIG. 12. Although three telescoping members are shown, it should be understood that two or more telescoping members can be included. The telescoping stiffening member 432 can provide varying levels of stiffening along its length based on the varying diameters of the telescoping members 442, 444, and 446. The telescoping stiffening member 432 can also provide varying levels of stiffening along its length by collapsing or expanding one or more of the telescoping members 442, 444 and 446. The telescoping stiffening member 432 can also provide stiffening along varied lengths of the elongate member 420 by collapsing or expanding one or more of the telescoping members 442, 444 and 446.

Figure 13A:
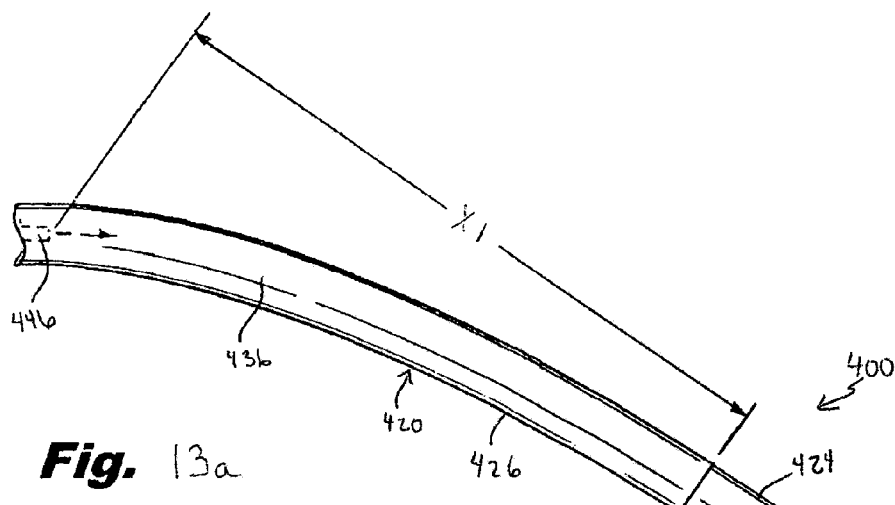
FIGS. 13a-13e are each a side view of a portion of the medical device of FIG. 11 showing a stiffening member at various different locations within an elongate member.
Figure 13B:
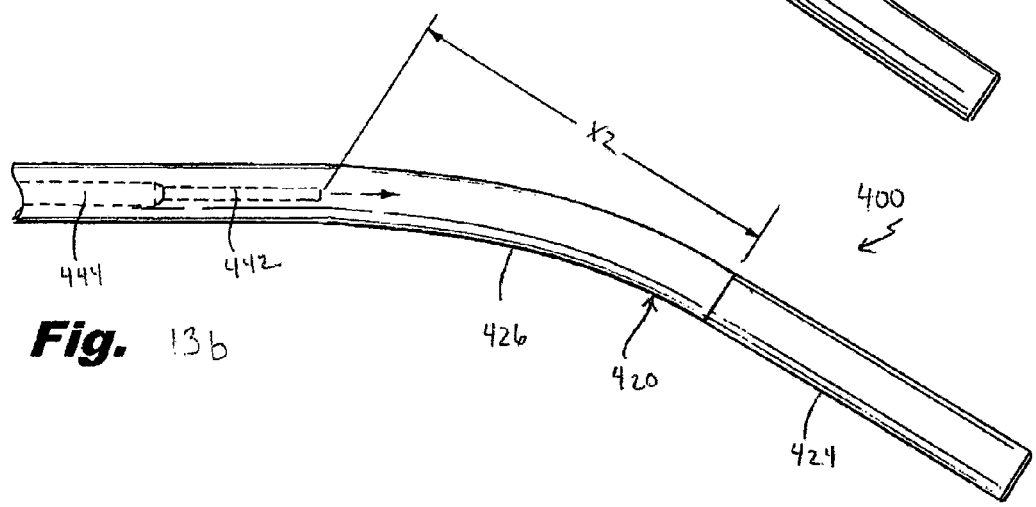
Figure 13C:
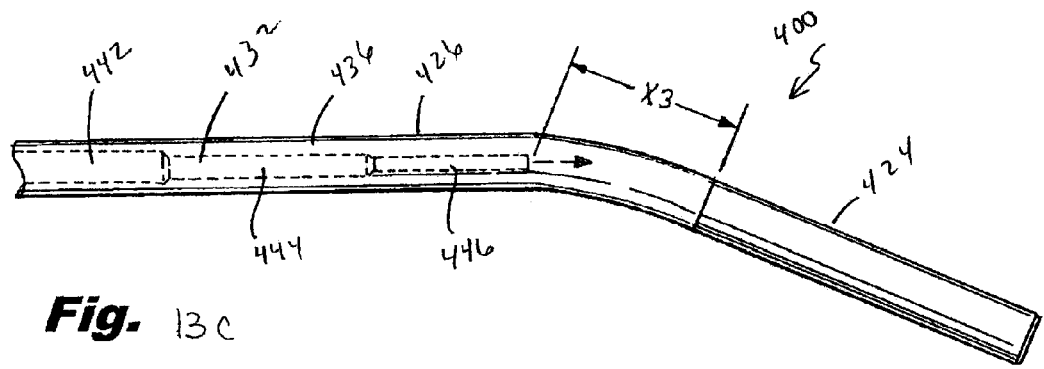
Figure 13D:
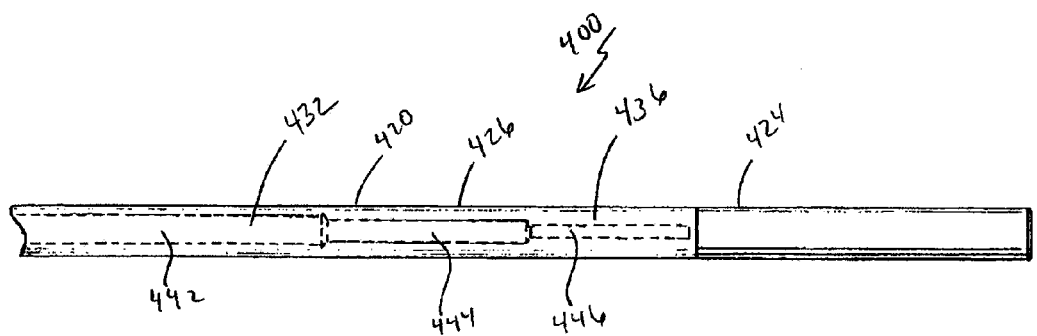
Figure 13E:
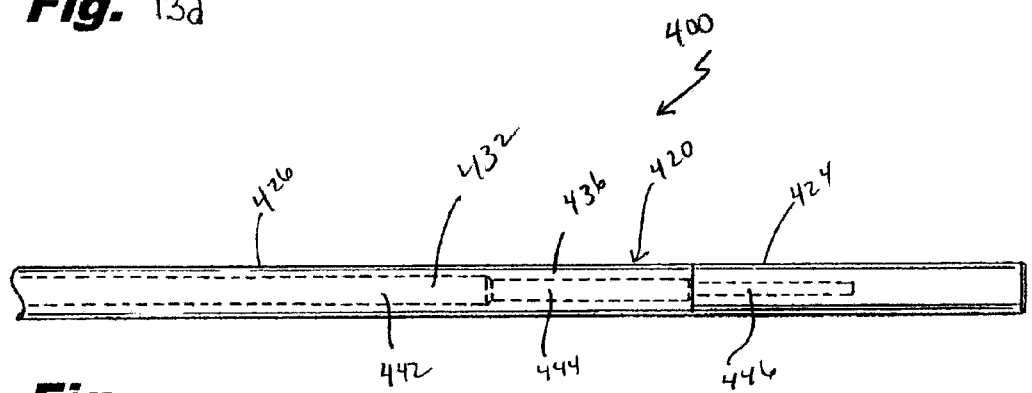

The stiffening member 432 can be inserted into the lumen 436 of the elongate member 420 and moved to a selected location within the lumen of the elongate member 420 to modify the flexibility (e.g., provide more rigidity or strengthen) of that selected portion of the elongate member 420 during insertion of the elongate member 420 into a body lumen of a patient. The stiffening member 432 can then be removed prior to insertion of another medical tool into the lumen 436 to perform a medical procedure. FIGS. 13a-13c each illustrate the stiffening member 432 disposed at various distances XI-X3 from the deflectable distal end portion 424. FIG. 13d shows the stiffening member 432 disposed just proximal of the distal end portion 424, and FIG. 13e illustrates the telescoping member 446 disposed within the distal end portion 424. In alternative embodiments, the telescoping stiffening member 432 can be inserted into a second lumen of the elongate member in a similar manner as described above for endoscope 300 and stiffening member 332.

FIGS. 14 and 15 illustrate another embodiment of an endoscope. An endoscope 500 includes an elongate member 520 having a distal end portion 524, a proximal end portion (not shown) and a medial portion 526. The elongate member 520 defines a lumen (not shown) between the proximal end portion and the distal end portion 524 that is in fluid communication with an opening (not shown) defined at a distal end 538 of the elongate member 520. As with previous embodiments, the lumen of the elongate member 520 can be used as a working channel for insertion of a medical tool. In this embodiment, a stiffening member 532 is slidably disposable along an exterior of the elongate member 520. The endoscope 500 can also include a handle (not shown) and an actuator (not shown) as described above for previous embodiments.

As with the previous embodiments, the distal end portion 524 is deflectable and can function in the same manner as the distal end portions 124, 224, 324, 424 previously described, and can be moved or articulated from a substantially linear or straight configuration (e.g., as shown in FIG. 15) to a variety of different curved or angled configurations (as shown in broken-line in FIG. 14) in a variety of different directions relative to a longitudinal axis of the elongate member 520.

In this embodiment, the stiffening member 532 has a sleeve configuration and defines a lumen 534 (see FIG. 16*a*) through which the elongate member 520 is received. The stiffening member 532 can be moved along the exterior of the elongate member 520 to a selected location along the length of the elongate member 520 to modify the flexibility of that selected portion of the elongate member 520. FIG. 14 illustrates the stiffening member 532 disposed at a first location and FIG. 15 illustrates the stiffening member 532 disposed just proximal of the distal end portion 524.

In an alternative embodiment, a stiffening member 532' can alternatively have a substantially c-shaped cross-section as shown in FIG. 16*b*. The stiffening member 532' can be slidably coupled to the exterior of an elongate member by inserting elongate member 520 along the opening of the "C" of the stiffening member 532', and function in a similar manner as described above for previous embodiments.

In some situations it may be desirable to provide a passive deflectable portion at a selected location along an elongate member of an endoscope. For example, FIG. 17 illustrates an endoscope 600 disposed within a kidney K. The endoscope 600 includes an elongate member 620 having a deflectable distal end portion 624, a medial portion 626 and a proximal portion 622. In this example, as the distal end portion 624 is being inserted into the kidney K, a portion of the medial portion 626 (proximal of the deflectable distal end portion 624) can contact an upper pole U of the kidney K and curve or bend away from the upper pole U (using the upper pole as support) as it is being inserted further distally. With an unhealthy kidney, however, because the collecting system may be distended, the upper pole may be deflected or moved away from the medial portion 626. In such a case, it may be more difficult to maneuver the distal portion 624 of the endoscope 600 around the curves of the kidney K.

Figure 18:
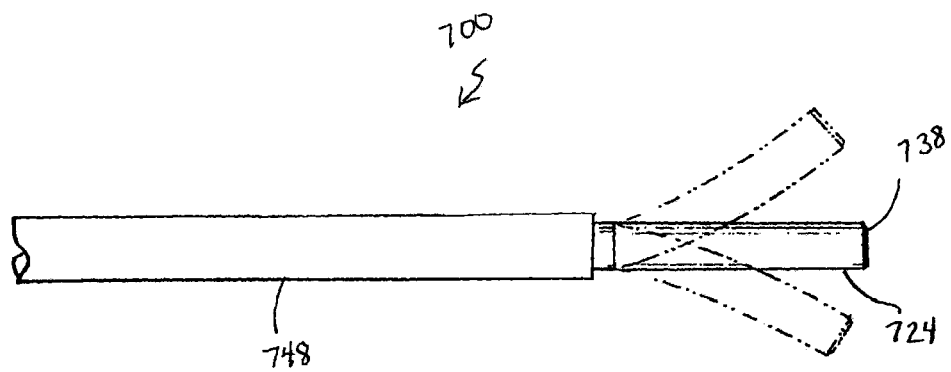
FIG. 18 is a side view of a portion of a medical device according to another embodiment, shown in a first configuration.
Figure 19:
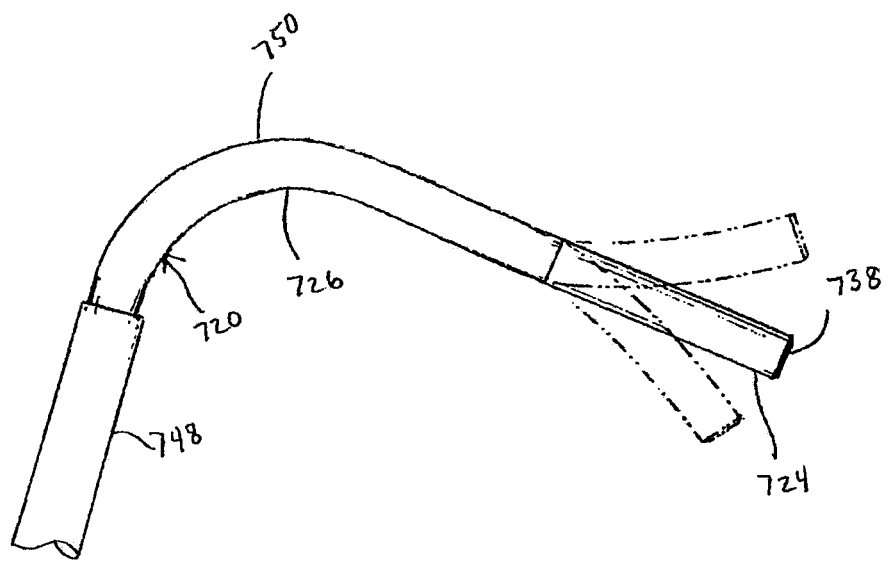
FIG. 19 is a side view of a portion of the medical device of FIG. 18 shown in a second configuration.

FIGS. 18 and 19 illustrate an embodiment of an endoscope that includes a shape-memory portion to provide a secondary or passive deflectable portion distal of the active deflectable distal end portion that can address the above described issue. An endoscope 700 includes an elongate member 720 having a secondary deflectable portion 750 disposed proximally of a deflectable distal end portion 724. The elongate member 720 has a distal end portion 724, a proximal end portion 722 (see FIG. 20) and a medial portion 726. As described above for previous embodiments, the elongate member 720 can define a lumen (not shown) between the proximal end portion 722 and the distal end portion 724 that is in fluid communication with an opening (not shown) defined at a distal end 738 of the elongate member 720. As with previous embodiments, the lumen of the elongate member 720 can be used as a working channel for insertion of a medical tool. The distal end portion 724 is deflectable and can function in the same manner as described above for other embodiments and can be moved or articulated from a substantially linear or straight configuration to a variety of different curved or angled configurations (shown in broken-line in FIGS. 18 and 19) in a variety of different directions relative to a longitudinal axis of the elongate member 720.

The secondary deflectable portion 750 can include some or all of a medial portion 726 of the elongate member 720. In some embodiments, the secondary deflectable portion can include the remaining portions of the elongate member 720. The endoscope 700 also includes a sheath 748 slidably disposed along an exterior of the elongate member 720, such that the elongate member 720 and the sheath 748 can be slidably moved relative to each other. For example, the elongate member 720 can be moved relative to the sheath 748 and/or the sheath 748 can be moved relative to the elongate member 720.

The secondary deflectable portion 750 can be formed with a shape-memory material such that the secondary deflectable portion 750 can be biased to a desired curved, angled or bent configuration. In some embodiments, the entire elongate member 720 can be formed with a shape-memory material. When the secondary deflectable portion 750 is unrestrained, it is free to assume its biased configuration. In this embodiment, the sheath 748 can be moved relative to the elongate member 720 such that the sheath 748 is disposed over the secondary deflectable portion 750 (or the elongate member 720 can be moved relative to the sheath 748). In this position, the sheath 748 restrains the secondary deflectable portion 750 and prevents it from moving to its biased configuration, as shown in FIG. 18. In some embodiments, the sheath 748 maintains the secondary deflectable portion 750 in a substantially linear configuration. The sheath 748 can be moved proximally such that the secondary deflectable portion is unrestrained and allowed to assume its biased configuration as shown in FIG. 19.

Figure 20:
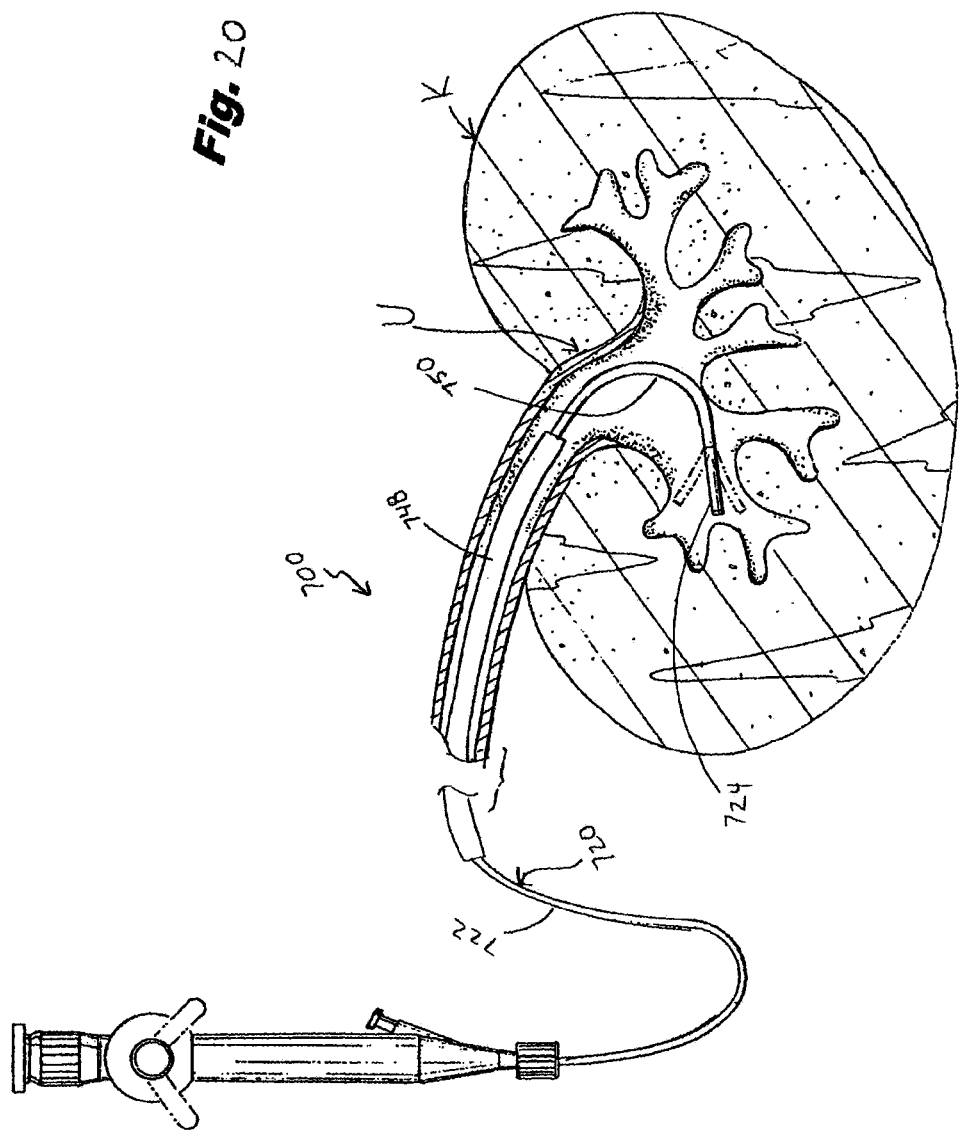
FIG. 20 is a side view of the medical device of FIGS. 18 and 19 shown disposed within a schematic representation of a kidney.

In use, the distal end portion 724 of the endoscope 700 can be inserted into a patient, such as into a kidney K, as shown in FIG. 20. During insertion, the sheath 748 can be positioned over the secondary deflectable portion 750 until the distal end portion 724 is disposed at a desired location. The sheath 748 can then be moved proximally such that the secondary deflectable portion 750 can assume its biased configuration (e.g., curved, angled or bent) while disposed within the kidney K. This allows the secondary deflectable portion 750 to automatically maneuver around the curves of the kidney without necessarily contacting the upper pole U of the kidney K. Thus, the performance of the endoscope is not affected by the condition of the kidney. As discussed above, this embodiment may be desirable when performing a medical procedure within an unhealthy or damaged kidney.

Figure 21:
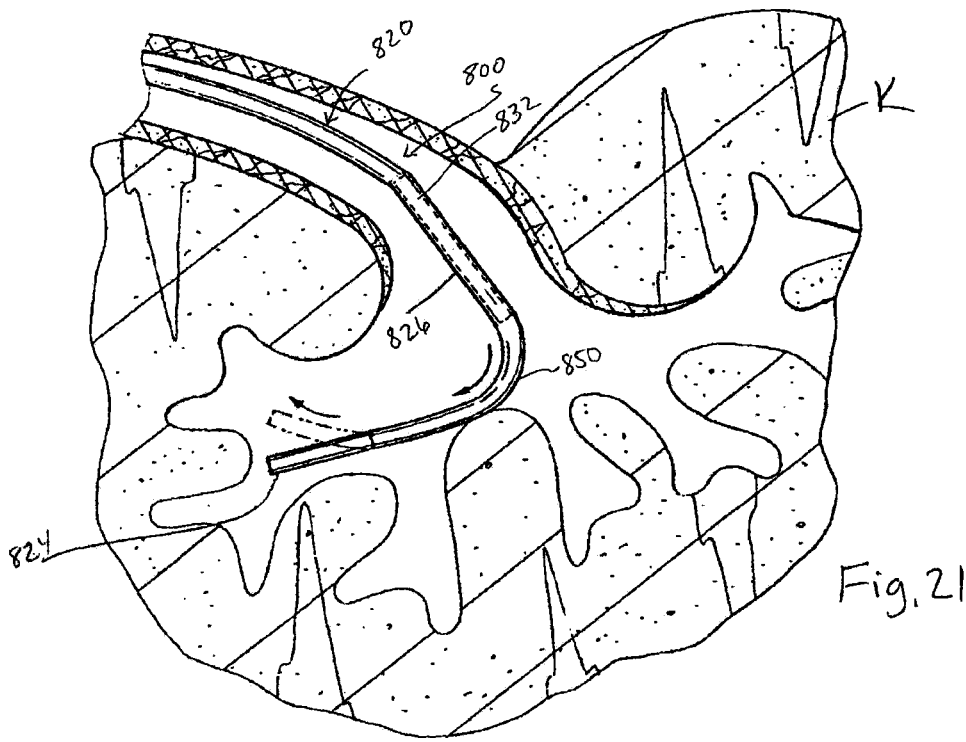
FIGS. 21-23 are each a side view of a portion of a medical device according to different embodiments shown partially disposed within a schematic representation of a kidney.
Figure 22:
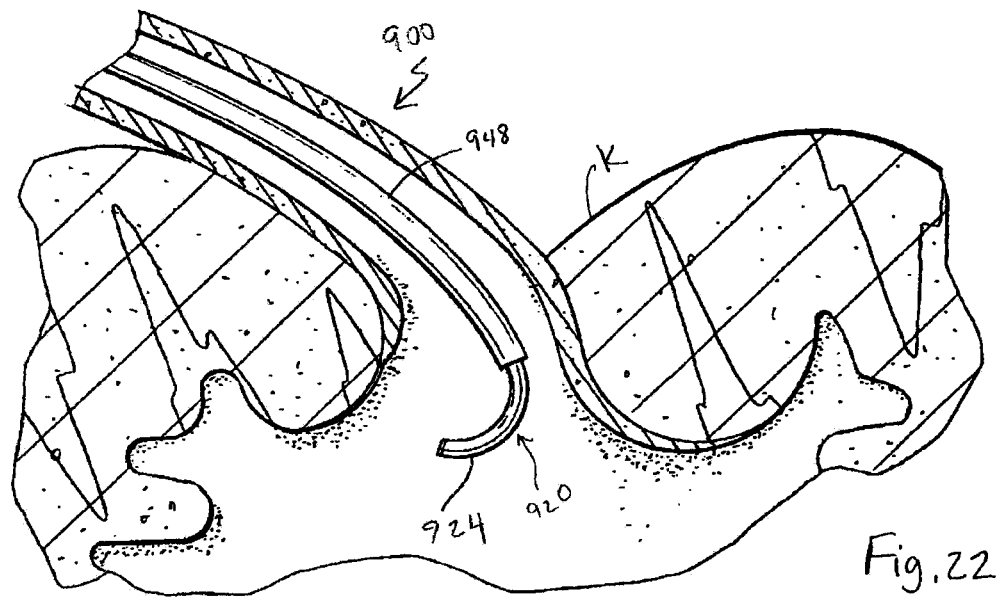
Figure 23:
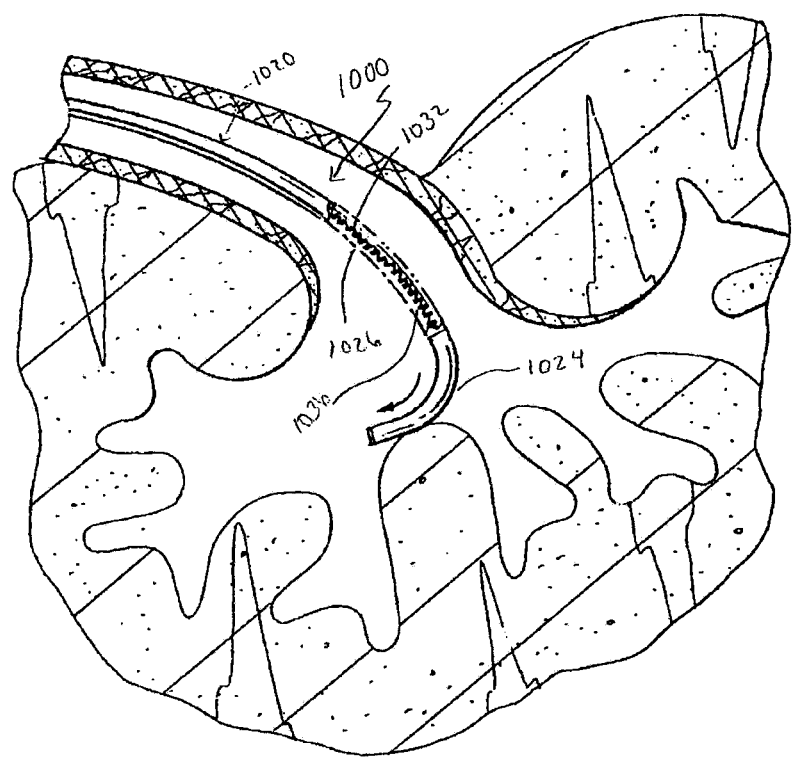

FIGS. 21-23 each illustrate an endoscope according to different embodiments shown with a portion of the endoscope disposed within a kidney K. Each of the embodiments of FIGS. 21-23 can include the various components as described above for previous embodiments and can perform in a similar manner as previously described. Thus, only certain aspects of the embodiments of FIGS. 21-23 are described below.

FIG. 21 illustrates an embodiment of an endoscope that includes a combination of a secondary deflectable portion and a stiffening member as described herein. An endoscope 800 includes an elongate member 820 having a proximal end portion (not shown), a medial portion 826 and an active deflectable distal end portion 824. The elongate member 820 includes a passive or secondary deflectable portion 850, shown in a biased curved configuration in FIG. 21. As described above, the secondary deflectable portion 850 can be a portion of the elongate member 820 formed with a shape-memory material. The secondary deflectable portion 850 can be restrained within a restraining member (not shown) such as a sheath (e.g., sheath 748) as described above with reference to endoscope 700. The endoscope 800 also includes a stiffening member 832 disposed within a lumen of the elongate member 820. The stiffening member 832 can be formed for example, similar to the stiffening member 232 in the form of a sleeve defining a lumen.

FIG. 22 illustrates an embodiment of an endoscope that includes an elongate member that is formed with a shape-memory material at a distal end portion of the elongate member. An endoscope 900 includes an elongate member 920 having a proximal end portion (not shown) a medial portion (not shown) and a passive deflectable distal end portion 924. The passive deflectable distal end portion 924 can be formed with a shape-memory material as described for previous embodiments. The endoscope 900 also includes a sheath 948 slidably disposed over the elongate member 920. The passive deflectable distal end portion 924 is shown in a biased curved configuration in FIG. 22 and can be moved to a restrained configuration when the sheath 948 is disposed over the passive deflectable distal end portion 924. Other portions of the elongate member 920 can be formed with a shape-memory material in addition to the passive deflectable distal end portion 924. For example, the medial portion of the elongate member 920 can also provide passive deflection. In alternative embodiments, the entire elongate member 920 can be formed with a shape-memory material to provide passive deflection along its length. The endoscope 900 can also optionally include a stiffening member as described herein.

FIG. 23 illustrates an embodiment of an endoscope that includes a stiffening member in the form of a coil or spring. An endoscope 1000 includes an elongate member 1020 having a proximal end portion (not shown) a medial portion 1026 and an active deflectable distal end portion 1024. The deflectable distal end portion 1024 can function in a similar manner as described above for previous embodiments of an active deflectable distal end portion (e.g., 124, 224 324, etc.). The endoscope 1000 also includes a stiffening member 1032 that can be inserted into a lumen 1036 of the elongate member 1020. The stiffening member 1032 is in the form of a coil or spring and can be moved to a selected location within the lumen 1036 of the elongate member 1020 to modify the flexibility during insertion of the elongate member 1020 into a body lumen of a patient. The stiffening member 1032 can then be removed prior to insertion of another medical tool into the lumen 1036 to perform a medical procedure. In alternative embodiments, the stiffening member 1032 can be inserted into a second lumen of the elongate member in a similar manner as described above for stiffening member 332 and endoscope 300.

The various embodiments of a medical device described herein (e.g., 100, 200, 300, 400, etc.) can be constructed with any suitable material used for such medical devices. For example, the various components of an endoscope can be formed with one or more biocompatible materials, such as silicone, nylon, polyglycolic acid, or stainless steel, and various polymers. The various components of an endoscope can be formed with various elastic materials, flexible materials, rubber materials, or combinations thereof. For example, the elongate members (e.g., 120, 220, 320, etc.), stiffening members (132, 232, 332, etc.), sheath (e.g., 748) can be formed, from soft, thin polyurethane, LLDPE, silicon, pellethane, polyurethane or other approved biocompatible materials, such as polyethylene, polypropylene or polyvinyl alcohol. In some embodiments, the elongate members (e.g., 120, 220, 320, etc.) can be formed with cuts or scoring along its length and/or width to provide for further flexibility.

In addition, various components of a medical device (e.g., endoscope) can be fabricated from extruded, molded, or machined plastic material(s), such as polypropylene, polycarbonate, or glass-filled polycarbonate. Some components may be made of stainless steel. Other suitable materials will be apparent to those skilled in the art.

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

For example, the medical devices described herein (e.g., 100, 200, 300, etc.) can include various combinations and/or sub-combinations of any of the components and/or features of the different embodiments described herein. For example, any of the embodiments of a medical device (e.g., endoscope) can include a secondary deflectable portion. Any of the embodiments can include a stiffening member (e.g., 132, 232, 332, etc.) in combination with a secondary deflectable portion (e.g., 750, 850). An endoscope according to the invention can have a variety of different shapes and sizes, and include a different quantity of lumens, and various different features and capabilities.

In addition, any of the embodiments of a stiffening member (e.g., 132, 232, 332, etc.) can be constructed with constant wall thickness and/or include a constant diameter (e.g., inner and/or outer diameter) or include varying wall thicknesses and/or varying diameters (e.g., inner and/or outer diameter) along its length.

Although various embodiments illustrated the use of the medical device for a medical procedure within a kidney, the medical devices described herein can be used within various other locations of a patient's body. For example, the medical devices can be used to perform a medical procedure in other organs, such as, a ureter, a gastrointestinal lumen, an esophagus, a vascular lumen, a colon, an esophagus, a stomach, a urethra, a bladder, lungs, bronchi, uterus, etc.

What is claimed:

1. An apparatus, comprising:
   a flexible elongate member that defines at least one lumen and is configured to be inserted within a body passageway of a patient, wherein the flexible elongate member includes a proximal portion, a distal portion, and a medial portion disposed between the proximal portion and the distal portion, and wherein the distal portion is movable between a substantially linear configuration and a curved configuration; and
   a stiffening member coupled to the flexible elongate member, the stiffening member being movable to a selected location along a length of the flexible elongate member to modify the flexibility of the selected location of the flexible elongate member, and wherein the stiffening member includes a first portion and a second portion, the first portion having a first stiffness and the second portion having a second stiffness different than the first stiffness, the first and second portion each configured to bias the flexible elongate member toward a straight configuration during use, wherein the stiffening member is disposed within, and slidable with respect to, the at least one lumen of the flexible elongate member, and the first portion includes a first sleeve and the second portion includes a second sleeve telescopically coupled to the first sleeve to provide varying levels of stiffening by selectively collapsing or expanding the telescopically coupled first and second sleeves.

2. The apparatus of claim 1, wherein the stiffening member includes a variable diameter along a length of the stiffening member.

3. The apparatus of claim 1, wherein the stiffening member includes a varying wall thickness along a length of the stiffening member.

4. An apparatus, comprising:
a flexible elongate member that defines at least one lumen and is configured to be inserted within a body passageway of a patient, wherein the flexible elongate member includes a proximal portion, a distal portion, and a medial portion disposed between the proximal portion and the distal portion, and wherein the distal portion is movable between a substantially linear configuration and a curved configuration; and
a stiffening member coupled to the flexible elongate member, the stiffening member being movable to a selected location along a length of the flexible elongate member to modify the flexibility of the selected location of the flexible elongate member, and wherein the stiffening member includes a first portion and a second portion, the first portion having a first stiffness and the second portion having a second stiffness different than the first stiffness,
wherein the stiffening member is disposed within, and slidable with respect to, the at least one lumen of the flexible elongate member, and
the first portion includes a first sleeve and the second portion includes a second sleeve telescopically coupled to the first sleeve to provide varying levels of stiffening by selectively collapsing or expanding the telescopically coupled first and second sleeves.

5. The apparatus of claim 4, wherein the stiffening member includes a variable diameter along a length of the stiffening member.

6. The apparatus of claim 4, wherein the stiffening member includes a varying wall thickness along a length of the stiffening member.

7. The apparatus of claim 4, wherein the stiffening member includes a third sleeve telescopically coupled to the first and second sleeves.

8. An apparatus, comprising:
a flexible elongate member that defines at least one lumen and is configured to be inserted within a body passageway of a patient, wherein the flexible elongate member includes a proximal portion, a distal portion having an active deflective portion to deflect the distal portion, and a medial portion disposed between the proximal portion and the distal portion, and wherein the distal portion is movable between a substantially linear configuration and a curved configuration; and
a stiffening member coupled to the flexible elongate member, the stiffening member being movable to a selected location along a length of the flexible elongate member to modify the flexibility of the selected location of the flexible elongate member, and wherein the stiffening member includes a first portion and a second portion, the first portion having a first stiffness and the second portion having a second stiffness different than the first stiffness, wherein the stiffening member is disposed within, and slidable with respect to, the at least one lumen of the flexible elongate member, and the first portion includes a first sleeve and the second portion includes a second sleeve telescopically coupled to the first sleeve to provide varying levels of stiffening by selectively collapsing or expanding the telescopically coupled first and second sleeves.

9. The apparatus of claim 8, wherein the stiffening member includes a variable diameter along a length of the stiffening member.

10. The apparatus of claim 8, wherein the stiffening member includes a varying wall thickness along a length of the stiffening member.

* * * * *